United States Patent [19]

Rzeszotarski et al.

[11] Patent Number: 5,049,555

[45] Date of Patent: Sep. 17, 1991

[54] ANTAGONISTS OF SPECIFIC EXCITATORY AMINO ACID RECEPTORS AS NEUROPROTECTANTS AND ANXIOLYTICS

[75] Inventors: Waclaw J. Rzeszotarski, Millersville; Maria E. Guzewska, Pasadena; Suzanne R. Ellenberger, Reisterstown; Lisa H. Conti, Baltimore; John W. Ferkany, Baltimore; Donald J. Kyle, Baltimore, all of Md.

[73] Assignee: Nova Pharmaceutical Corporation, Baltimore, Md.

[21] Appl. No.: 286,153

[22] Filed: Dec. 19, 1988

[51] Int. Cl.$^5$ .............................................. A61K 31/66
[52] U.S. Cl. .................................................... 514/114
[58] Field of Search ......................................... 514/114

[56] References Cited

U.S. PATENT DOCUMENTS 4,657,899 4/1987 Rzeszotarski et al. .............. 514/114
4,761,405 8/1988 Rzeszotarski et al. .............. 514/114

Primary Examiner—Stanley J. Friedman
Attorney, Agent, or Firm—Vincent L. Fabiano

[57] ABSTRACT

The invention pertains to a method and pharmaceutical compositions for treating, preventing or reducing neurodegeneration associated with chronic central nervous system or hypoxic, ischemic and hypoglycemic injury to the central nervous system and for the treatment of anxiety through the use of 2-amino-ω-phosphonoalkanoic acids having a cycloalkyl group bridging adjacent carbons on the alkyl chain, their pharmaceutically acceptable salts and derivatives as neuroprotectants and anxiolytics.

19 Claims, No Drawings

ANTAGONISTS OF SPECIFIC EXCITATORY AMINO ACID RECEPTORS AS NEUROPROTECTANTS AND ANXIOLYTICS

BACKGROUND OF THE INVENTION

1. Field of the Invention

The invention pertains to a method of treating or preventing neuronial damage through the potent neuroprotectants and anxiolytics which achieve their action through the antagonism of specific excitatory amino acid (EAA) neurotransmitter receptors. More particularly, the invention is directed to the use of 2-amino-$\omega$-phosphonoalkanoic acids bearing a cycloalkyl group bridging adjacent carbons on the alkyl chain and their pharmaceutically acceptable salts and derivatives, as neuroprotectants and anxiolytics.

2. Description of the Prior Art

Three major types of receptors for excitatory amino acids (EAA) have been identified in the mammalian central nervous system (CNS). Originally designated according to agonist responses, these include sites activated by the pyrrolidine neurotoxin kainic acid, the conformationally restricted glutamate analog, quisqualic acid and the synthetic aspartate analog, N-methyl-D-aspartic acid (NMDA) [Watkins and Evans, R. H.: Excitatory Amino Acid Transmitters. Ann. Rev. Pharmacol. Toxicol. 21:165-204, 1981; Foster and Fagg, Acidic Amino Acid Binding In Mammalian Neuronal Membranes: Their Characteristics And Relationships to Synaptic Receptors. Br. Res. Rev. 7:103-184, 1984; Ferkany, Receptors For Excitatory Amino Acids: Ligand Binding and Functional Assays. In Receptor Pharmacology and Function, ed. by M. Williams, R. Glennon and B. M. Timmermans, Marcel Dekker, Inc., New York, N.Y. pp. 415-452, 1988]. Specific and potent antagonists of EAA-mediated neurotransmission have been identified only for the latter recognition site and, accordingly, our understanding of the functional role of NMDA receptors in physiological and pathological conditions is most advanced.

To date, NMDA receptors have been implicated in a variety of CNS processes including learning and memory [Morris et al., Selective Impairment of Learning and Blockade of Long-Term Potentiation by an N-Mehtyl-D-Aspartate Receptor Antagonist, AP5. Nature 319:774-776, 1986; Pontecorvo and Clissold, NMDA Antagonism and Working Memory Performance. Soc. Neurosci. Abs. 14:101.2, 1988: epilepsy [Croucher et al., Anticonvulsant Action of Excitatory Amino Acid Antagonists. Science 216:899-901, 1982: Schwarcz and Ben-Ari, eds. Excitatory Amino Acids and Epilepsy, Plenum Press, New York, N.Y., 1986], nociception [Raigordsky and Urca, Intrathecal N-Methyl-D-Aspartate (NMDA) Activates Both Nociceptive and Antinociceptive Systems. Br. Res. 422:158-162, 1987], neurodegenerative disorders [Foster et al., On the Excitotoxic Properties of Quinolinic Acid, 2,3-Piperidine Dicarboxylic Acids and Structurally Related Compounds. Neuropharmacol. 22:1331-1342, 1983: Greenamyre et al., Alterations in L-Glutamate Binding Sites in Alzheimer's and Huntington's Diseases. Science 227:1496-1499, 1984: Young et al., NMDA Receptor Losses in Putamen From Patients With Huntington's Disease. Science 241:981-983, 1987], dementia [Greenamyre et al., Dementia of the Alzheimer's Type: Changes in Hippocampal L-[3H]Glutamate Binding. J. Neurochem. 48:543-551, 1987: Geddes et al., Density and Distribution of NMDA Receptors in the Human Hippocampus in Alzheimer's Disease. Br. Res. 399:156-161, 1986], and the neuronal damage seen following hypoxia [Goldberg et al., N-Methyl-D-Aspartate Receptors Mediate Hypoxic Neuronal Injury in Cortical Culture. J. Pharmacol. Exp. Therap. 243:784-791, 1987: Clark and Rothman, Blockade of Excitatory Amino Acid Receptors Protects Anoxic Hippocampal Slices. Neurosci. 21:665-671, 1987], ischemia [Simon, et al., Blockade of N-Methyl-D-Aspartate Receptors May Protect Against Ischemic Damage in the Brain. Science 226:850-852, 1984] and hypoglycemia [Weiloch, Hypoglycemia-Induced Neuronal Damage Prevented By An N-Methyl-D-Aspartate Antagonist. Science 230:681 683, 1985].

Given this breadth of function, the proposal that NMDA receptor antagonists may provide a novel therapeutic method to intervene in CNS pathology is not surprising. However what is surprising is that prototypical antagonists such as DL($\pm$)2-amino-5-phosphonopentanoic acid and DL($\pm$)2-amino-7-phosphonoheptanoic acid, while proving useful to explore the basic characteristics of NMDA receptor-mediated neurotransmission, lack the potency and bioavailability to be useful in a clinical setting.

More recently, two approaches to develop therapeutically acceptable antagonists have been pursued. First, is the development of noncompetitive antagonists which inhibit neuroexcitation at either the NMDA receptor-associated ion channel [Anis et al., The Dissociative Anaesthetics Ketamine and Phencyclidine Reduce Excitation of Central Mammalian Neurons by N-Methyl Aspartate. Brit. J. Pharmacol. 79:565-575, 1983; Jarvis, et al., Quantitative Autoradiographic Localization of NMDA Receptors in Rat Brain Using [3H]CPP: Comparison With [3H]TCP Binding Sites. Eur. J. Pharmacol. 141:148-152, 1987] or the glycine-activated modulatory site [Johnson and Ascher, Glycine Potentiates the NMDA Response in Cultured Mouse Brain Neurons. Nature 325:529-531, 1987; Kleckner and Dingledine, Requirement for Glycine in Activation of NMDA Receptors Expressed in Xenopus Oocytes. Science 241:835-837, 1988]. Second, using the method of rational design, attempts have been made to develop potent, selective, competitive antagonists having substantial CNS bioavailability following systemic administration. Each approach has yielded promising compounds including the noncompetitive antagonist MK-801 [5-methyl-10,11-dihydro-5H-dibenzo[a,d]cyclohepten-5,10-imine] [Clineschmidt, et al., Anticonvulsant Activity of (+)-5-Methyl-10,11-Dihydro-5H-Dibenzo[a,d] Cyclohepten-5, 10 Imine (MK-801), a Substance With Potent Anticonvulsant, Central, Sympathomimetic, and Apparent Anxiolytic Properties. Drug Dev. Res. 2:123-134, 1982; Wong et al., The Anticonvulsant MK-801 is a Potent N-Methyl-D-Aspartate Antagonist. Proc. Nat. Acad. Sci. (USA) 83:7104-7108, 1986; Kemp, et al., Non-Competitive Antagonists of Excitatory Amino Acid Receptors. Tr. Neurosci. 10:294-298, 1987], as well as the competitive receptor blockers CPP [3-(2-carboxypiperazin-4-yl) propyl-1-phosphonic acid] [Olverman, et al., [3H]CPP, A New Competitive Ligand for NMDA Receptors. Eur. J. Pharmacol. 131:161-162, 1986; Lehmann, et al., A Selective N-Methyl-D-Aspartate (NMDA)-Type Receptor Antagonist: Characterization in Vitro and in Vivo. J. Pharmacol. Exp. Therap. 240:737-746, 1987; Chapman, et al., Anticonvulsant Action and Biochemical Effects in DBA/2 Mice of CPP (3-(+)-2-carboxypiperazin-4-yl)-propyl-1-phosphonate), A Novel N-Methyl-D-Aspartate Antagonist. Eur. J. Pharmacol. 139:91–96,1987], CGS 19755 [4-phosphonomethyl-2-piperidinecarboxylic acid] [Boast, et al., A Comparison of Two N-Methyl-D-Aspartate Antagonists. See. Neurosci. Abs. 13:497, 1987; Lehmann, et al., CGS 19755, A Selective and Competitive N-Methyl-D-Aspartate-Type Excitatory Amino Acid Receptor Antagonist. J. Pharmacol Exp. Therap. 246: 1988] and [2-amino-4,5-(1,2-cyclohexyl)-7-phosphonoheptanoic acid [Ferkany et al., submitted]. For example, it has been shown in U.S. Pat. No. 4,761,405 and Ferkany, et al., Pharmacological Profile of NPC 12626, A Novel, Competitive N-Methyl-D-Aspartate Receptor Antagonist, J. Pharmac. Exp. Ther. (Submitted), that [NPC 12626] 2-amino-4,5-(1,2-cyclohexyl)-7-phosphonoheptanoic acid selectively inhibits ligand binding to NMDA receptors in vitro and that the compound is a potent anticonvulsant in animal models of epilepsy.

SUMMARY OF THE INVENTION

The present invention pertains to a method to treat, prevent or reduce the neuronal damage that occurs following hypoxic or ischemic insult to the CNS by administering potent and selective antagonists, or their pharmaceutically acceptable salts, of specific receptors for excitatory amino acids. The invention also describes a method to treat anxiety using these same compounds and a method to treat, prevent or reduce the neurodegeneration associated with acute or chronic diseases of the CNS. Specifically the invention employs antagonists having the general Formula I:

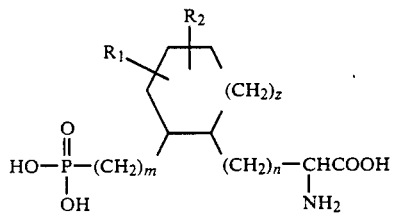

wherein $R_1$ and $R_2$ are the same or different and are selected from the group consisting of hydrogen, lower alkyl [$C_1$ to $C_6$], alkyl [$C_7$ to $C_{12}$], fatty acid chain [$C_{13}$ to $C_{24}$], aryl, aralkyl, hydroxyl, carbonyl and the derivatives thereof, the stereoisomers being in their resolved or racemic form; n and m=0, 1, 2 or 3; Z=0, 1 or 2 cycloalkyl ring being replaced with the cycloalkenyl ring; and the pharmaceutically acceptable salts and derivatives thereof.

DETAILED DESCRIPTION OF THE INVENTION

The invention pertains to the use of potent, selective and specific NMDA-receptor antagonists to prevent, treat or reduce neurodegeneration associated with chronic CNS disorders, hypoxic of ischemic insult to the CNS and hypoglycemic insult to the CNS. Additionally, the use of potent and selective NMDA receptor antagonists to treat anxiety is described.

As the above compounds contain both an amino function and a carboxylic function, it will be appreciated that these compounds can exist as a zwitterion. In addition, the formation of salts involving either the amino group or the carboxylic acid group of these dipolar molecules is possible by respective use of acids having a pKa below that of the carboxylic acid group.

The compounds of this invention may be used in the form of a pharmaceutically acceptable acid addition salt having the utility of the free base. Such salts, prepared by methods well known to the art, are formed with both inorganic or organic acids, for example: Maleic, fumaric, benzoic, ascorbic, pamoic, succinic, bismethylenesalicylic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric, and nitric acids. The compounds of this invention may also be used as acceptable base addition salts, i.e. salts with bases having a pKa above that of the amino groups, e.g., sodium, potassium, etc. While the compounds of this invention are herein depicted by Formula I above, it is to be appreciated that the full range of the invention embraces the various ionized forms thereof as well.

Since these molecules are asymmetric and may further exist in either the cis or trans configuration, four different isomeric forms are possible. Thus the present invention embraces both the d- and l-cis isomers and the d- and l-trans isomers. The cis and trans forms are prepared by different chemical syntheses while the d- and l-isomer of either the cis or trans form can be resolved by the classical methods, as for example, by formation of diastereomers.

The compounds of this invention may be administered orally or parenterally in conventional dosage unit forms such as tablets, capsules, injectables or the like, by incorporating the appropriate dose of a compound of Formula I, with carriers according to accepted pharmaceutical practices. Preferably a compound or an acid or base addition salt thereof is administered orally to an animal organism in a tablet or capsule comprising an amount sufficient to produce excitatory amino acid inhibitory activity. Each dose unit will contain the active medicament in an amount of about 0.5 mg to about 500 mg preferably about 1 mg to about 40 mg. Advantageously equal doses will be administered 2 to 4 times daily with the daily dosage regimen being about 1 mg to about 320 mg, preferably about 2 mg to about 160 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and other such carriers known to those skilled in the art. Exemplary of liquid carriers are syrup, peanut oil, olive oil, water and other such carriers known to those skilled in the art. Similarly the carrier or diluent can include any time delay material well known to the art, such as glyceryl monostearate or glyceryl distearate alone or with a wax. Such preparations may also be formulated into suppositories for rectal administration.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg to about 1 mg. If a liquid carrier is used, the preparation will be in the form of a syrup, emulsion, soft gelatin capsule, sterile injectable liquid such as an ampule, or an aqueous or non aqueous liquid suspension.

Of particular applicability is an aerosol dispensing system wherein the active medicament is incorporated with Freon (fluorohydrocarbon) or other inert propellant in an aerosol container. Such an aerosol system will deliver a metered dose of about 50 meg to about 1600 meg administered as needed.

EXAMPLE I

Prevention of Excitatory Amino Acid Agonist-induced Neurodegeneration

Injection of EAA receptor agonists into the brain, including agonists for kainic acid, quisqualic acid and NMDA receptors produces a stereotypic axon-sparing lesion wherein neurons having soma adjacent to the injection site are destroyed. In contrast, axons of neurons distant to the injection, but which pass through the region of the injection, are spared. The lesion is similar to that observed postmortem in the brains of patients dying with degenerative disorders of the CNS (e.g., Huntington's Disease), and the procedure has been used to develop animal models of dementia. The discovery that the potent NMDA agonist, quinolinic acid, occurs endogenously in the brain has further strengthened the suggestion that EAA neurotransmission may be involved in degenerative disorders of the CNS.

For the study, adult male Sprague-Dawley rats (175-250 g; Charles Rivers) were anesthetized with Chloropent (4 ml/kg) and placed in a David-Kopf stereotaxic apparatus. A 0.3 mm stainless steel cannula was lowered into the corpus striatum through a small burr hole in the calvarium; coordinates for the injection were A 0.8, L 3.0 and V 4.4 (midline, bregma and dura=0.0). Kainic acid was dissolved in saline (0.9%; w/v); all other drugs were dissolved in distilled water. Solutions were adjusted to neutral pH using NaOH, and 1 $\mu$l of the solution containing kainic acid (10 nm) or quinolinic acid (300 nm) with or without the compounds of the invention (150 nm) was infused over a period of 60 seconds. Following a further delay of 60 seconds, the cannula was slowly retracted and the scalp apposed with autoclips.

Following a three day recovery period, animals were sacrificed by decapitation, the corpus striatum was dissected, weighed and frozen ($-80°$ C.) until assay. The extent of neuronal damage was determined by measurement of choline acetyltransferase (ChAT) and glutamic acid decarboxylase (GAD), specific markers for striatal interneurons. For assay, striatal tissues were homogenized in 50 mM Tris-HCl buffer (pH 7.4; 23° C.) containing 0.2% (w/v) Triton-X-100. After centrifugation at 10,000 g for 10 minutes (23° C.), a portion of the supernatant was assayed for ChAT activity by the method of Bull and Oderfeld-Nowak Standization of a Radiochemical Assay of Choline Acetyltransferse and a Study of the Activation of the Enzyme in Rabbit Brain. J. Neurochem. 19:935-947, (1971), or for GAD activity according to the method of Wilson et al., Markers For Gene Expression In Cultured Cells From Nervous System. J. Biol. Chem. 247:3159-3169, 1972. Protein content of the samples was determined as described by Bradford A Rapid And Sensitive Method For Quantitation Of Microgram Quantities of Protein Utilizing The Principle of Protein Dye Binding. Anal. Biochem. 72:248-254, (1976).

As shown in Table 1, intrastriatal injection of kainic acid or quinolinic acid produced a significant decline in the activities of ChAT and GAD relative to the contralateral striatum. Like ($\pm$)CPP, (150 nm), 2-amino-4,5-(1,2-cyclohexyl)-7-phosphonoheptanoic acid (NPC 12626) (150 nm) significantly attenuated the neurotoxic effects of quinolinic acid to the extent that there was no difference in enzyme activities between tissues ipsilateral and contralateral to the site of injection. In contrast, 2-amino-4,5-(1,2-cyclohexyl)-7-phosphonoheptanoic acid (150 nm) had no neuroprotective effect on kainic acid-induced neurodegeneration.

TABLE 1

EFFECTS OF COMPETITIVE NMDA RECEPTOR ANTAGONISTS ON QUINOLINIC ACID- AND KAINIC ACID-INDUCED STRIATAL NEURODEGENERATE

| TREATMENT | N | PERCENT CONTRALATERAL STRIATUM | |
|---|---|---|---|
| | | ChAT | GAD |
| Quinolate | 14 | 53 $\pm$ 6* | 40 $\pm$ 12* |
| Plus NPC 12626 | 6 | 97 $\pm$ 6 | 98 $\pm$ 2 |
| Plus ($\pm$) CPP | 7 | 98 $\pm$ 3 | 99 $\pm$ 4 |
| Kainate | 7 | 34 $\pm$ 5* | 44 $\pm$ 8* |
| Plus NPC 12626 | 6 | 35 $\pm$ 10* | 46 $\pm$ 1* |

*significantly different from contralateral striatum, P $\leq$ 0.05,

The values represent the percent enzyme activity in the injected striatum as a function of the tissues contralateral to the injection site. Values are the mean$\pm$S.E.M. of the indicated number of animals.

Student's two tailed t-test. NPC 12626=2-Amino-4,5-(1,2-cyclohexyl)-7-phosphonoheptanoic acid The results of the current study demonstrate that 2-amino-4,5-(1,2-cyclohexyl)-7-phosphonoheptanoic acid is a potent antagonist of the endogenous. NMDA-like neurotoxin, quinolinic acid. Furthermore, the results indicate that the action of 2-amino-4,5-(1,2-cyclohexyl)-7-phosphonoheptanoic acid is specific to an interaction with NMDA-type receptors in brain since the compound did not prevent the neurotoxic effect of kainic acid.

EXAMPLE II

Protection Against Ischemia-induced Brain Damage

Competitive and non-competitive NMDA antagonists are useful to prevent CNS damage following ischemic insult to the brain. The current invention evaluated 2-amino-4,5-(1,2-cyclohexyl)-7-phosphonoheptanoic acid for utility as a neuroprotectant following global ischemic insult in gerbils.

Male Mongolian gerbils (50-70 g) were anesthetized using halothane:oxygen:nitrogen (4:40:56, induction: 2:40:58, maintenance) and a small incision was made bilaterally in the neck to expose the carotid arteries. Ligatures were inserted through one barrel of a double barreled polypropylene cannula, passed under the arteries and passed again through the alternate barrel. The skin was apposed with suture and the ligatures were loosely tied-off. In some instances, the femoral vein of the animal was cannulated simultaneously to facilitate intravenous administration of the test compounds. One day post surgery, conscious animals were subjected to a 5 minute period of ischemia by applying tension to both ligatures. During and after the ischemic episode, body temperature was measured with a rectal probe and was maintained at 37° C. using heat lamps. Test compounds were dissolved in saline and the solutions adjusted to neutrality. Compounds were administered as indicated in the legend of Table 2.

Three days following ischemia animals were sacrificed by decapitation and the brains processed for light microscopic examination. The extent of neuronal damage to the $CA_1$ region of the hippocampus was determined using an arbitrary rating scale as follows:

0 = no observable damage,
1 = 0 to 10% neurons damaged,
2 = 10–25% neurons damaged,
3 = 25–50% neurons damaged,
4 = 50 to 75% neurons damaged,
5 = >75% neurons damaged.

Preliminary evaluations indicated a high degree of interobserver reliability in rating. For all experiments, observers were blind to the treatment associated with the sections being scored.

The noncompetitive NMDA antagonist (+)MK-801 (3 mg/kg), the competitive antagonist (±)CPP (5 mg/kg) and 2-amino-4,5-(1,2-cyclohexyl)-7-phosphonoheptanoic acid (100 mg/kg) afforded virtually complete protection to $CA_1$ hippocampal neurons when the compounds were administered intraperitoneally 30 minutes prior to, and 10 and 60 minutes following a 5 minute episode of ischemia (Table 2). When administered intraperitoneally 10 and 60 minutes following the insult, neither (±)CPP (10 mg/kg) nor 2-amino-4,5-(1,2-cyclohexyl)-7-phosphonoheptanoic acid (25–100 mg/kg) were effective in this regard (Table 2). However, when 2-amino-4,5-(1,2-cyclohexyl)-7-phosphonoheptanoic acid (25 mg/kg) was administered intravenously via the femoral vein 10 minutes and 60 minutes following bilateral carotid occlusion, significant neuroprotective actions were recorded. (±)MK-801 (3 mg/kg) but not (±)CPP (10 mg/kg) was also an effective neuroprotectant by this route of administration. Additionally, administration of a single bolus of 2-amino-4,5-(1,2-cyclohexyl)-7-phosphonoheptanoic acid (25 mg/kg) immediately after the insult followed by the constant infusion of an additional 50 mg/kg (iv) over a period of 90 minutes, elicited a neuroprotective response (Table 2).

The results from the current example are important since they demonstrate the utility of 2-amino-4,5-(1,2-cyclohexyl)-7-phosphonoheptanoic acid (NPC 12626) as a neuroprotective agent following ischemic insult to the CNS. Furthermore, the data differentiate the compound from the piperazine, (±)CPP since under identical conditions, the latter competitive NMDA antagonist did not provide neuroprotection when administered solely after the ischemic episode.

TABLE 2

EFFECT OF NMDA ANTAGONISTS ON NEURONAL DAMAGE IN THE $CA_1$ REGION OF THE HIPPOCAMPUS FOLLOWING GLOBAL ISCHEMIA

| COMPOUND | N | DOSE (mg/kg) | NEUROPROTECTIVE INDEX |
|---|---|---|---|
| Pre- and Post-Ischemic Intraperitoneal Administration | | | |
| CONTROL | 21 | | 3.7 ± 0.36 |
| (+) MK)801 | 6 | 3 | 1.1 ± 0.08* |
| NPC 12626 | 11 | 100 | 0.9 ± 0.27* |
| (±)CPP | 10 | 5 | 1.8 ± 0.34* |
| Post-Ischemic Intravenous Administration | | | |
| CONTROL | 21 | | 3.6 ± 0.25 |
| (+) MK-801 | 10 | 3 | 1.1 ± 0.27* |
| NPC 12626 | 40 | 25 | 2.2 ± 0.32* |
| (±)CPP | 8 | 10 | 5.0 ± 0.0 |
| Post-Ischemic Constant Intravenous Infusion | | | |
| CONTROL | 8 | | 3.6 ± 0.62 |
| NPC 12626 | 7 | 25,50 | 1.8 ± 0.83* |

Surgical methods have been described in the text. In the pre-and post-ischemic condition, compounds were administered (ip) at the indicated dose 30 minutes prior to, and 10 and 60 minutes following, a 5 minute period of global ischemia. For the post-ischemic condition, compounds were administered (iv) at the indicated dose, 10 and 60 minutes following the insult. For the constant infusion procedure, NPC 12626 was administered (25 mg/kg; iv) as a bolus 10 minutes after the ischemic insult followed by the constant infusion (1 µl/minute; 0.5 mg/kg/minute; 50 mg/kg total dose) of drug for an additional 90 minutes.

The values are the mean±S.E.M. of scores from the indicated number of subjects.

EXAMPLE III

Prevention of Hypoxia-induced Mortality

Several psychoactive agents including pentobarbital and diazepam are known to increase the survival time of animals exposed to a hypoxic environment. Additionally, compounds that increase hypoxic survival time may be useful in protecting against conditions of anoxia in humans such as those associated with surgical interventions, anemias, or accidental exposure to hypoxic environments.

To test the effects of 2-amino-4,5-(1,2-cyclohexyl)-7-phosphonoheptanoic acid and other compounds on hypoxic survival, adult male CF-1 mice (25–35 g) were injected (ip) with vehicle or drug. Thirty minutes later, groups of mice were placed in a one liter sealed plexiglass container. The atmosphere in the chamber was rapidly replaced with a mixture of nitrogen:oxygen (96%:4%) using a pressurized delivery system. The hypoxic conditions were maintained at equilibrium by continually exhausting the atmosphere to a fume hood with constant, pressurized replacement of the gas mixture.

Results are shown in Table 3. Notably, both the noncompetitive NMDA antagonist, (+) MK-801, and the competitive NMDA antagonists, (±) CPP and 2-amino-4,5-(1,2-cyclohexyl)-7-phosphonoheptanoic acid extended hypoxic survival time in a dose-dependent manner. The results are important since they suggest excitatory amino acid antagonists may represent novel therapeutic agents useful in preventing hypoxic or anoxic injury to the CNS.

TABLE 3

MEAN HYPOXIC SURVIVAL TIME FOR ANIMALS TREATED WITH EXCITATORY AMINO ACID RECEPTORS ANTAGONISTS

| DRUG | DOSE (mg/kg) | MEAN SURVIVAL TIME (seconds ± S.E.M.) | # SURVIVING SIX MINUTES # TESTED |
|---|---|---|---|
| Vehicle | — | 155 ± 5 3 | 0/56 |
| (+) MK-801 | 0.3 | 150 ± 24 | 0/8 |
| | 3.0 | 277 ± 28* | 2/8 |
| (±)CPP | 5 | 201 ± 24 | 0/8 |
| | 10 | 253 ± 28* | 1/8 |
| NPC 12626 | 25 | 243 ± 18* | 0/8 |
| | 50 | 264 ± 26* | 2/8 |
| | 100 | 274 ± 31* | 3/8 |

Values represent the number of seconds male CP-1 mice survived exposure to an hypoxic environment. The test was terminated at 300 seconds. Animals surviving for this period were given a score of 300; the number of animals surviving to 300 seconds is shown in the far right column.

EXAMPLE IV

Anxiolytic activity.

Other reports (see description of prior art) suggest that competitive and noncompetitive NMDA antagonists may have non-benzodiazepine receptor-mediated anxiolytic activity in animal models. The compounds may, thus, provide a new approach to the treatment of stress and anxiety states in man.

In the first method, the procedure of Pellow, et al. Validation of Open: Closed Arm Entries in an Elevated Plus-Maze as a Measure of Anxiety in the Rat. J. Neurosci. Meth. 14:149-167, (1985) was used with the exception that test subjects were male CF-1 mice (25-35 g). Compounds were administered intraperitoneally in a 10% solution of Tween 80 and saline 30 minutes prior to assay. Animals were placed in the middle of two perpendicular arms of an elevated plus-maze which was 50 cm above the floor. Two opposing arms (50×10×40 cm; L, W, H) of the maze were shielded with walls and the two remaining arms (50×10 cm; L, W) were open to the test environment. Typically, vehicle treated animals spend a large amount of time in the shielded portion of the maze; diazepam and other benzodiazepines increase both the number of entries by animals into the open arms as well as the amount of time animals spent in the open arms. Animals were scored for the percentage of time spent in the open arms as well as the percentage entries into the open arms during a 5 minute observation period.

In a second procedure, rats (Sprague-Dawley; Charles Rivers; 200-350 g) were administered (ip) the compounds of interest in a 10% solution of Tween 80 and saline 30 minutes prior to being placed in to a standard conditioning chamber (Colbourne Instruments model #E10-10SF). Two minutes later the animals received a mild scrambled footshock (0.5 mA 0.55 seconds) followed 30 seconds later by a second shock. Following the second shock, animals were observed for a period of 4 minutes; typically, vehicle treated animals spent the majority of the session in a frozen, defensive posture. Compounds having anxiolytic activity dose-dependently decrease the amount of time the animal spends in this immobilized state.

In the elevated plus-maze procedure, 2-amino-4,5-(1,2-cyclohexyl)-7-phosphonoheptanoic acid (12.5 and 35 mg/kg; ip) produced a significant [$F(1, 14)=6.44$, $p \leq 0.05$; ANOVA] increase in the percentage of open arm entries compared to vehicle (Table 4). Likewise, animals given 35 mg/kg spent a greater percentage of time in the open arms than vehicle injected mice [$F (1, 14)=2.93$, $p \leq 0.10$] although this difference was not statistically significant. The effects of diazepam and (±) CPP on open arm activity are also shown on Table 4. Diazepam at 1 mg/kg [$F (1, 14)=5.22$, $P \leq 0.05$] or 4 mg/kg [$F (1, 14)=11.21$, $p \leq 0.02$] significantly increased the percentage of time drug-treated animals spent in the open portion of the maze. However, even at 4 mg/kg, the percentage of open arm entries was not different from control animals [$F (1, 14)=4.05$, $p \leq 0.06$]. (±) CPP, at doses up to 5 mg/kg had no effect on elevated plus-maze performance.

TABLE 4

EFFECT OF EXCITATORY AMINO ACID RECEPTOR ANTAGONISTS AND DIAZEPAM ON THE ELEVATED PLUS MAZE PERFORMANCE OF CF-1 MICE

| Compound | N | % Time in Open Arms (Mean ± S.E.M.) | % Entries into Open Arms (Mean ± S.E.M.) |
|---|---|---|---|
| Diazepam | | | |
| Vehicle | 8 | 11.0 ± 4.6 | 15.8 ± 7.6 |
| 1 mg/kg | 8 | 27.0 ± 5.2* | 23.2 ± 4.8 |
| 2 mg/kg | 8 | 16.0 ± 6.4 | 16.0 ± 6.3 |
| 4 mg/kg | 8 | 42.4 ± 8.3* | 40.7 ± 9.8 |
| NPC 12626 | | | |
| Vehicle | 8 | 13.2 ± 16.1 | 10.8 ± 12.7 |
| 6.25 mg/kg | 8 | 7.0 ± 7.7 | 14.1 ± 16.1 |
| Vehicle | 8 | 10.3 ± 9.1 | 20.8 ± 21.6 |
| 12.5 mg/kg | 8 | 26.0 ± 21.7 | 36.1 ± 21.2* |
| Vehicle | 8 | 38.4 ± 10.6 | 28.6 ± 7.3 |
| 35 mg/kg | 8 | 60.6 ± 7.4* | 47.7 ± 4.9* |
| CPP Vehicle | 8 | 19.8 ± 5.4 | 20.0 ± 5.5 |
| CPP | | | |
| 1.25 mg/kg | 8 | 30.6 ± 6.0 | 31.4 ± 4.2 |
| 2.5 mg/kg | 8 | 22.6 ± 4.6 | 19.3 ± 3.6 |
| 5.0 mg/kg | 8 | 22.5 ± 6.5 | 25.3 ± 14.4 |

*$P \leq 0.05$ ANOVA
NPC 12626 = 2-Amino-4,5-(1,2-cyclohexyl)-7-phosphonoheptanoic acid.

The values represent (1) the percentage of time that animals spent in open arms of elevated plus maze as a function of total observation time or (2) the percentage of entires animals made into the open arms of the maze as a function of total entires into any arm of the maze.

Like diazepam (25 mg/kg) and (±)CPP (5 mg/kg), 2-amino-4,5-(1,2-cyclohexyl)-7-phosphonoheptanoic acid (6.25, 12.5 and 25 mg/kg) significantly decreased the amount of time rats spent immobilized in the foot-shock-induced freezing test (Table 5).

The data demonstrate that 2-amino-4,5-(1,2-cyclohexyl)-7-phosphonoheptanoic acid functions like an anxiolytic in two animal models. While less potent than diazepam or (±)CPP, 2-amino-4,5-(1,2-cyclohexyl)-7-phosphonoheptanoic acid displayed anxiolytic activity at non-sedating doses. Few clinically useful drugs other than the benzodiazepines exhibit this profile in most animal models of anxiety. Consistent with other studies, the data suggest that 2-amino-4,5-(1,2-cyclohexyl)-7-phosphonoheptanoic acid may represent an additional and novel chemical class of anxiolytic agent.

Furthermore, the compound is different from (±) CPP since 2-amino-4,5-(1,2-cyclohexyl)-7-phosphonoheptanoic acid, but not (±) CPP produces anxiolytic effects in the elevated plus-maze text. NPC 12626 is also different from the noncompetitive antagonist (+) MK-801 since (+) MK-801 did not have anxiolytic activity in the foot-shock-induced freezing paradigm.

TABLE 5

EFFECT OF EXCITATORY AMINO ACID RECEPTOR ANTAGONISTS AND DIAZEPAM OR FOOTSHOCK-INDUCED FREEZING IN RATS

| COMPOUND | N | MIN SPENT IN FREEZE POSTURE (MEAN ± S.E.M.) |
|---|---|---|
| Diazepam | | |
| VEHICLE | 16 | 2.50 ± .30 |
| 1.25 mg/kg | 16 | 2.03 ± .34 |
| 2.5 mg/kg | 15 | 1.58 ± .34* |
| 5.0 mg/kg | 14 | 1.23 ± .32* |
| NPC 12626 | | |
| VEHICLE | 12 | 2.26 ± .33 |
| 3.12 mg/kg | 7 | 1.59 ± .66 |
| 6.25 mg/kg | 7 | 2.49 ± .46 |
| 12.5 mg/kg | 7 | 1.06 ± .38* |

TABLE 5-continued
EFFECT OF EXCITATORY AMINO ACID RECEPTOR ANTAGONISTS AND DIAZEPAM OR FOOTSHOCK-INDUCED FREEZING IN RATS

| COMPOUND | N | MIN SPENT IN FREEZE POSTURE (MEAN ± S.E.M.) |
|---|---|---|
| 25.0 mg/kg | 7 | 0.75 ± .25* |
| (±)CPP | | |
| VEHICLE | 15 | 2.04 ± .33 |
| 1.25 mg/kg | 16 | 1.32 ± .29 |
| 2.5 mg/kg | 16 | 1.35 ± .31 |
| 5.0 mg/kg | 16 | 1.10 ± .33* |
| (+) MK-801 | | |
| VEHICLE | 10 | 2.54 ± .30 |
| 0.05 mg/kg | 9 | 2.89 ± .28 |
| 0.10 mg/kg | 9 | 2.71 ± .35 |
| 0.15 mg/kg | 9 | 2.02 ± .38 |

*P ≦ 0.05 ANOVA
NPC 12626 - 2-Amino-4,5-(1,2-cyclohexyl)-7-phosphonoheptanoic acid.

Values represent the amount of time animals spent in an immobilized defensive posture during a 4 minute observation period following application of 2 mild footshocks.

From the foregoing description, one of ordinary skill in the art can easily ascertain the essential characteristics of the instant invention, and without departing from the spirit and scope thereof, can make various changes and/or modifications of the invention to adapt it to various usages and conditions. As such these changes and/or modifications are properly, equitably and intended to be, within the full range of equivalence of the following claims.

What is claimed is:

1. A method for treating, preventing or reducing neurodegeneration associated with ischemic insult, anoxic insult, or hypoxia comprising administering a therapeutically effective amount of an excitatory amino acid neurotransmitter antagonist of the formula:

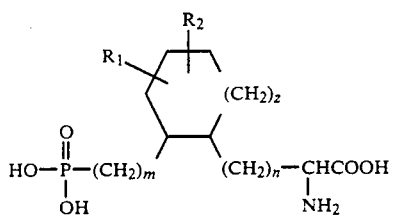

wherein $R_1$ and $R_2$ are the same or different and are selected from the group consisting of hydrogen, lower alkyl, alkyl, fatty acid chain, aryl, aralkyl, hydroxy, the stereoisomers being in their resolved or racemic form; amino, nitro, trifluoromethyl or cyano; n and m = 0, 1, 2 or 3 and Z = 0, 1 or 2; the cycloalkyl ring being replaced with the cycloalkenyl ring; and the pharmaceutically acceptable salts and derivates thereof to an animal in need thereof.

2. The method of claim 1 wherein said antagonist is 2-amino-4,5-(1,2-cyclohexyl)-7-phosphonoheptanoic acid.

3. The method of claim 1 wherein said antagonist is 2-amino-5,6-(1,2-cyclohexyl)-7-phosphonoheptanoic acid.

4. The method of claim 1 for treating, preventing or reducing damage to the central nervous system following ischemic insult to the central nervous system which comprises administering an effective amount of the compound with a pharmaceutically acceptable carrier and/or diluent.

5. The method of claim 4 for treating, preventing or reducing damage to the central nervous system following ischemic insult to the central nervous system which comprises administering an effective amount of one or more of compounds of claim 1 parenterally, nasally, orally, rectally or a combination thereof to said animal in need thereof.

6. The method of claim 4 for treating, preventing or reducing damage to the central nervous system following ischemic insult to the central nervous system wherein said compound is administered in an aerosol dispensing system containing an inert propellant.

7. The method of claim 6 for treating, preventing or reducing damage to the central nervous system following ischemic insult to the central nervous system wherein said inert propellant is Freon.

8. The method of claim 1 for treating, preventing or reducing damage to the central nervous system following anoxic insult to the central nervous system which comprises administering an effective amount of the compounds with a pharmaceutically acceptable carrier and/or diluent.

9. The method of claim 8 for treating, preventing or reducing damage to the central nervous system following anoxic insult to the central nervous system which comprises administering an effective amount of the compound parentally, nasally, orally, rectally or a combination thereof to said animal in need thereof.

10. The method of claim 8 for treating, preventing or reducing damage to the central nervous system following anoxic insult to the central nervous system wherein said compound is administered in an aerosol dispensing system containing an inert propellant.

11. The method of claim 10 for treating, preventing or reducing damage to the central nervous system following anoxic insult to the central nervous system wherein said inert propellant is Freon.

12. The method of claim 1 for treating, preventing or reducing damage to the central nervous system following hypoxic insult to the central nervous system which comprises administering an effective amount of the compound with a pharmaceutically acceptable carrier and/or diluent.

13. The method of claim 12 for treating, preventing or reducing damage to the central nervous system following hypoxic insult to the central nervous system which comprises administering an effective amount of the compound parenterally, orally, nasally, rectally or a combination thereof to said animal in need thereof.

14. The method of claim 12 for treating, preventing or reducing damage to the central nervous system following hypoxic insult to the central nervous system wherein said compound is administered in an aerosol dispensing system containing an inert propellant.

15. The method of claim 14 for treating, preventing or reducing damage to the central nervous system following hypoxic insult to the central nervous system wherein said inert propellant is Freon.

16. The method of claim 1 for preventing neurodegeneration which comprises administering an effective amount of the compound with a pharmaceutically acceptable carrier and/or diluent.

17. The method of claim 16 for preventing neurodegeneration which comprises administering an effective amount of the compound parenterally, orally, nasally, rectally or a combination thereof to said animal in need thereof.

18. The method of claim 16 for treating, preventing or reducing damage to the central nervous system following neurodegeneration wherein said compound is administered in an aerosol dispensing system containing an inert propellant.

19. The method of claim 18 for treating, preventing or reducing damage to the central nervous system following neurodegeneration wherein said inert propellant is Freon.

* * * * *